(12) United States Patent
Moorman

(10) Patent No.: US 11,376,376 B2
(45) Date of Patent: Jul. 5, 2022

(54) VARIABLE TEMPERATURE VAPORIZER TANK

(71) Applicant: Wallace Dray Moorman, Pompano Beach, FL (US)

(72) Inventor: Wallace Dray Moorman, Pompano Beach, FL (US)

(*) Notice: Subject to any disclaimer, the term of this patent is extended or adjusted under 35 U.S.C. 154(b) by 440 days.

(21) Appl. No.: 16/671,145

(22) Filed: Oct. 31, 2019

(65) Prior Publication Data

US 2020/0128879 A1 Apr. 30, 2020

Related U.S. Application Data

(60) Provisional application No. 62/753,074, filed on Oct. 31, 2018.

(51) Int. Cl.
*A24F 40/46* (2020.01)
*A61M 11/04* (2006.01)

(52) U.S. Cl.
CPC ... *A61M 11/041* (2013.01); *A61M 2205/3368* (2013.01)

(58) Field of Classification Search
CPC ......... A61M 11/041; A61M 2205/3368; A24F 40/42; A24F 40/46; A24F 40/20
See application file for complete search history.

(56) References Cited

U.S. PATENT DOCUMENTS

| | | | |
|---|---|---|---|
| 11,253,001 B2* | 2/2022 | Atkins | A24F 40/10 |
| 2017/0006917 A1* | 1/2017 | Alvarez | A24F 40/42 |
| 2017/0127723 A1* | 5/2017 | Wu | A24F 40/44 |
| 2017/0367404 A1* | 12/2017 | Li | H05B 1/0244 |
| 2019/0380387 A1* | 12/2019 | Rose | H05B 3/06 |
| 2021/0274843 A1* | 9/2021 | Trzecieski | A24F 40/10 |

* cited by examiner

*Primary Examiner* — Truc T Nguyen
(74) *Attorney, Agent, or Firm* — Allen F. Bennett; Bennett Intellectual Property

(57) ABSTRACT a variable temperature vaporizer accessory has a ceramic cup located within a base that can be attached to a mod type vaporizer. The ceramic cup is surrounded by a housing which has a mouthpiece at its distal end opposite the base. A biased press plate is configured to push down on material within the ceramic cup. A heating element within the base abuts the ceramic cup. The temperature within the ceramic cup may be attenuated. The ceramic cup and the housing defined and insulating air pocket. An air pocket in the bottom of the ceramic cup separates a vaporizing chamber from the hottest region of the vaporizing cup and heats incoming air.

5 Claims, 3 Drawing Sheets

VARIABLE TEMPERATURE VAPORIZER TANK

CROSS-REFERENCE TO RELATED APPLICATIONS

This application claims priority to U.S. Provisional Application Ser. No. 62/753,074 filed on Oct. 31, 2018, the contents of which are hereby incorporated in their entirety.

STATEMENT REGARDING FEDERALLY SPONSORED RESEARCH OR DEVELOPMENT

Not Applicable.

THE NAMES OF PARTIES TO A JOINT RESEARCH AGREEMENT

Not Applicable

INCORPORATION-BY-REFERENCE OF THE MATERIAL SUBMITTED ON A COMPACT DISC

Not Applicable.

COPYRIGHT NOTICE

Not Applicable

BACKGROUND OF THE INVENTION

Field of the Invention

The present invention relates to a vaporizer tank. More particularly, the invention relates to a vaporizer tank providing improved vapor when actuated.

Description of the Related Art

There are a large variety of vaporizer tanks on the market. A vaporizer tank attached to a mod vaporizer preferably minimizes combustion of the material being vape and produces vapor substantially by heating the material. Existing vaporizer tanks have and atomizer comes in the direct contact with the material being vaporized. This creates unwanted residue and also reduces the quality of the vapor.

The above-described deficiencies of today's systems are merely intended to provide an overview of some of the problems of conventional systems, and are not intended to be exhaustive. Other problems with the state of the art and corresponding benefits of some of the various non-limiting embodiments may become further apparent upon review of the following detailed description.

In view of the foregoing, it is desirable to provide an improved vaporizer tank.

BRIEF SUMMARY OF THE INVENTION

Disclosed is a vaporizer tank having a base. The base has a sleeve extending upward from its top and having one or more O-rings. A bolt extending downward from a bottom side, the bolt being engageable with a mod type vaporizer. A housing having an outer wall capable of forming a friction fit when extended over the sleeve of the base. A bracket within the housing affixed to a mouthpiece at a distal end of the housing. A press plate extends downward from the bracket and having a downward bias. A ceramic cup within the sleeve has a rim with a circumference greater than a circumference of the press plate.

It is therefore an object of the present invention to provide an improved variable temperature vaporizer tank.

These and other objects and advantages of the present invention will become apparent from a reading of the attached specification and appended claims. There has thus been outlined, rather broadly, the more important features of the invention in order that the detailed description thereof that follows may be better understood, and in order that the present contribution to the art may be better appreciated. There are features of the invention that will be described hereinafter and which will form the subject matter of the claims appended hereto.

BRIEF DESCRIPTION OF THE SEVERAL VIEWS OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
FIG. 1 is a perspective view of a variable temperature vaporizer accessory in accordance with the principles of the invention.

The invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The disclosed subject matter is described with reference to the drawings, wherein like reference numerals are used to refer to like elements throughout. In the following description, for purposes of explanation, numerous specific details are set forth in order to provide a thorough understanding of the various embodiments of the subject disclosure. It may be evident, however, that the disclosed subject matter may be practiced without these specific details. In other instances, well-known structures and devices are shown in block diagram form in order to facilitate describing the various embodiments herein. Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

Unless otherwise indicated, all numbers expressing quantities of ingredients, dimensions reaction conditions and so forth used in the specification and claims are to be understood as being modified in all instances by the term "about". The term "a" or "an" as used herein means "at least one" unless specified otherwise. In this specification and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Disclosed is a vaporizer tank having a combustion chamber and a mouthpiece which is readily attachable to a "mod" type vaporizer. The vaporizer tank is an advanced dry herb and concentrate vaping device having an improved gold-plated spring-loaded 510 connector, a ceramic plate shaped like a bowl to better hold dry materials, and improved airflow and power. All of the parts of the vaporizer tank can be detached and reassembled, increasing the convenience and ease of cleaning and maintenance. The completely ceramic combustion chamber results in no actual combustion of the material placed with in it. It is simply heated sufficiently to generate vapor without unwanted oxidation products. The heating element is not exposed to the combustion chamber and the ceramic plate heats the material with in it quickly and evenly.

FIGS. 1-7 show a vaporizer tank 10 in accordance with the principles of the invention. FIG. 1 shows the fully assembled vaporizer tank 10 having a base 12, a housing 14 and a mouthpiece 16. The base 12 has two air inlets 13. A threaded bolt 18 on the bottom 20 of the base 12 is configured to threadably engage a port in a standard "vape mod" vaporizer.

Figure 2:
FIG. 2 is another perspective view of a variable temperature vaporizer accessory in accordance with the principles of the invention.
Figure 3:
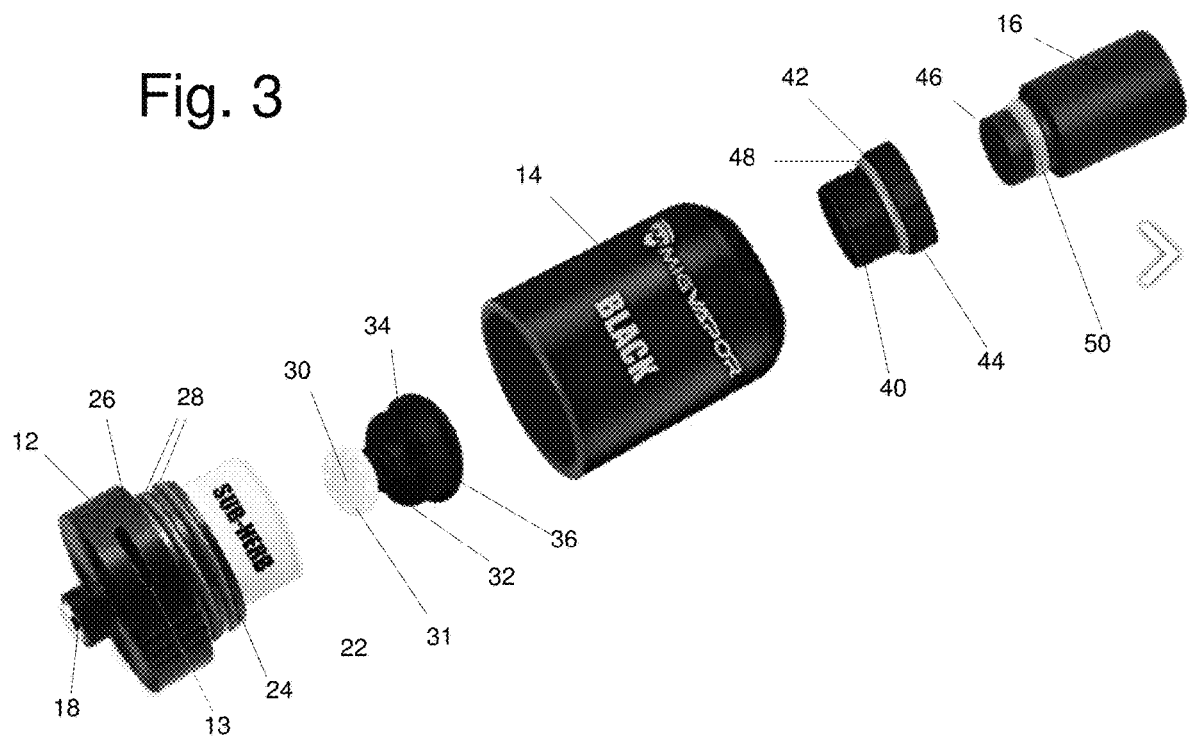
FIG. 3 is an exploded view of a variable temperature vaporizer accessory in accordance with the principles of the invention.

FIG. 2 shows the vaporizer tank 10 where the base 12 has been removed and FIG. 3 shows an exploded view of the vaporizer tank 10. A ceramic cup 22 has a cylindrical outer wall and a flat bottom. The ceramic cup 22 is seated inside a cylindrical sleeve 24 extending upward from the top 26 of the round base 12. Two O-rings 28 are positioned within two grooves about the circumference of the sleeve 24.

Figure 4:
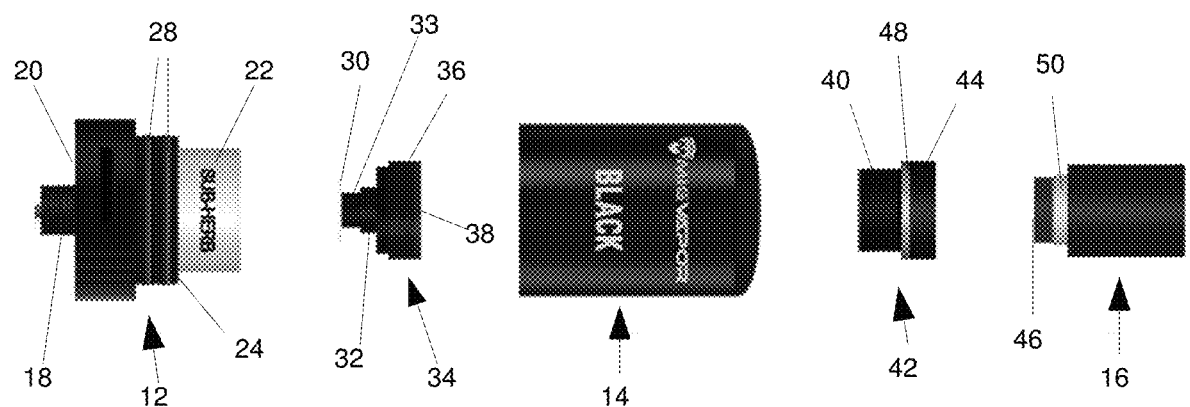
FIG. 4 is another exploded view of a variable temperature vaporizer accessory in accordance with principles of the invention.
Figure 6:
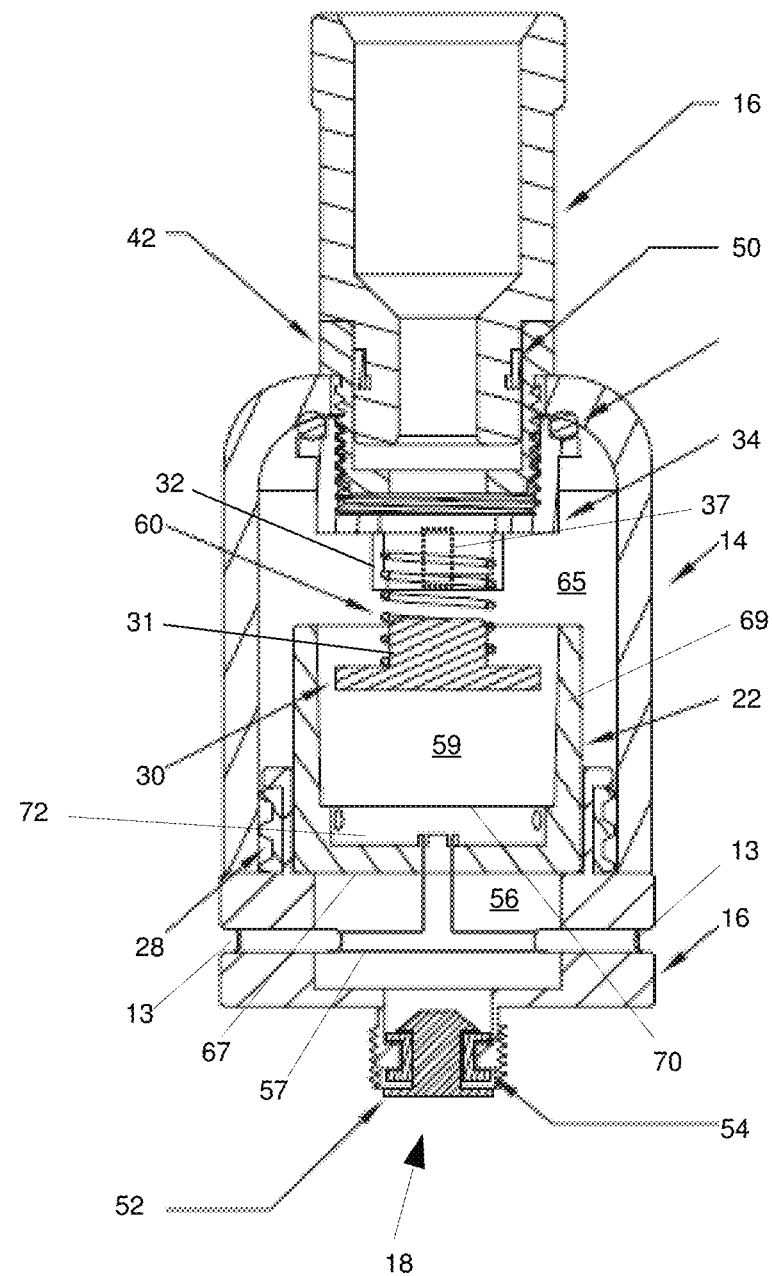
FIG. 6 is a cross-sectional view of a variable temperature vaporizer accessory in accordance with principles of the invention.

As shown in FIGS. 3 and 4, a press plate 30 affixed to the end of a cylindrical post 33 extends downward out of a cuff 32 from the bottom of a bracket 34 and is biased in a downward direction by a spring (shown in FIG. 6). In one embodiment, the press plate 30 is a ceramic disc having a plurality of holes 31 extending about its circumference, and is biased by a spring 60 (also shown in FIG. 6). The cylindrical body 36 of the bracket 34 has an upper internally threaded cuff 38 which threadably engages the externally threaded cuff 40 extending downward from the top seat 42. The top seat 42 has an upper internally threaded cuff 44 which threadably engages the lower externally threaded cuff 46 of the mouthpiece 16. The top seat 42 includes a gasket 48, and the mouthpiece 16 includes a gasket 50.

Figure 5:
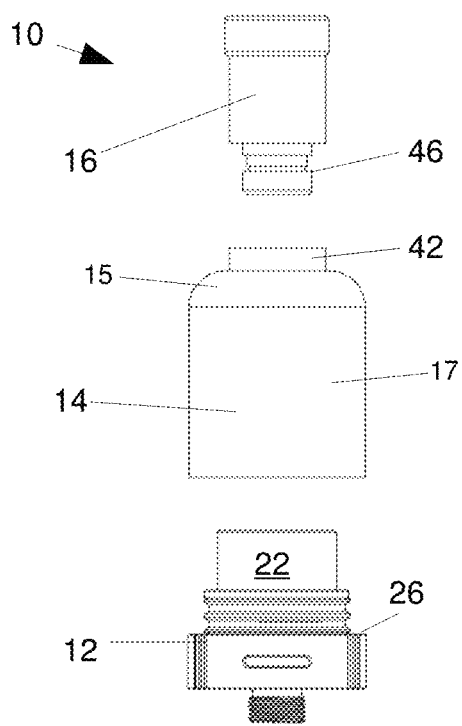
FIG. 5 is a side elevation view of a variable temperature vaporizer accessory in accordance with the principles of the invention.

FIG. 5 shows the vaporizer tank 10 partially assembled. The housing 14 is comprised of a hemispherical top 15 and a cylindrical wall 17. The top seat 42 extends through a hole in the hemispherical top 15 of the housing 14. Such that it externally threaded cuff 40 is inside the housing 14. The upper internally threaded cuff 44 of the top seat 42 is too wide to fit through the opening in the top of the housing 14. The mouthpiece 16 is removably attachable to the top seat 42 by engaging the mouthpieces externally threaded cuff 46 with the internally threaded cuff 48 of the top seat 42. The base is removably attached to the housing 14 by means of a friction fit between the O-rings and the inside of the cylindrical wall 17 of the housing 14.

FIG. 6 shows a cross-section of the assembled vaporizer tank 10. The mouthpiece 16 screws into the top seat 42, forming a tight seal by means of the gasket 50. The top seat 42 engages the bracket 34 through the hole in the housing 14. A spring 60 biases the post 33 and ceramic plate 30 downward out of the cuff 32. The cuff 32 includes one or more slits 37 that allows air to pass through the cuff 32 and upward out of the seat 42 and mouthpiece 16.

The bolt 18 extending downward from the base 16 includes an electrode 52 that extends over the distal end of the bolt 18. The electrode 52 also extends inward inside the bolt 18 and is surrounded by a silicone ring 54. The base 12 houses an electrically powered heating element 56 which abuts the bottom 67 of the ceramic cup 22. The housing 14 of this embodiment is removably attachable to the sleeve 24 by means of a friction fit with the O-rings 28. The bracket 34 is positioned inside the housing 14 and engages the top seat 40 such that the gasket 48 forms a seal with the housing 14. A thin, air permeable ceramic screen 70 creates a small air pocket 72 in the bottom of the ceramic cup 22 and separates the air pocket 72 from the vaporizing chamber 59. In this embodiments, the housing 14 is opaque. Optionally, the housing 14 may optionally be made of clear glass.

In use, a material used to produce vapor is placed in the vaporizing chamber 59 defined by the bottom 67 and cylindrical sidewall 69 of the cup 22. The bracket 34 is placed at the top of the inside of the housing 14 and threadably engages the top cap 42. The housing is then placed over the sleeve 24 to form a friction fit with the O-rings 28. When this occurs, the press plate 30, preferably formed from ceramic, impinges on the material within the vaporizing chamber 59 defined by the ceramic cup 22. The sleeve 24 has a larger diameter than the cup 22. When the housing 14 is placed over the sleeve 24, it forms an air pocket 65 between the ceramic cup 22 and the walls of the housing 14. This air pocket 65 acts as an insulator between the housing 14 and the vaporizing chamber 59 within cup 22.

The vaporizer tank 10 is screwed onto a mod type vaporizer. When the vaporizer is actuated, the heating element heats the ceramic cup 22, generating vapor. An operator places his or her mouth over the distal end of the mouthpiece 16 and inhales, sucking air through the mouthpiece 16. This negative pressure draws air through inlets 13 and air inlet channels 57. The heating element heats this air as it travels through the air inlet channels 57 and the air pocket 65 underneath the vaporizing chamber 59. Air then travels into the vaporizing chamber 59 where it mixes with vapors created by the material placed in the cup 22 as the vaporizing chamber 59 is heated by the ceramic cup 22.

The screen 70 and her pocket 72 separate the vaporizing chamber 59 from the bottom 67 of the cup 22. The bottom 67 is the only portion of the ceramic cup 22 that is in direct contact with the heating element 56 and is therefore the hottest region of the cup 22. By separating the vaporizing chamber 59 from the hottest region of the ceramic cup 22 oxidation and combustion of material within the vaporizing chamber 59 is minimized, such that the material within the vaporizing chamber 59 vaporizes more cleanly and fewer harmful oxidation products are formed and inhaled by a user.

The excess heat of the bottom 67 of the cup 22 is not wasted, because it heats the air flowing through the air pocket 72. The vaporized material then travels through the holes 31 and the ceramic plate 30 and up through the slits 37, through the seat 42 and the mouthpiece 16 into the mouth of a user. The air pocket 65 acts as an insulator between the housing 14 and the ceramic cup 22. Because the air pocket 65 is also exposed to negative air pressure caused by a user inhaling, the insulating properties of the air pocket 65 are increased. This prevents a user from accidentally burning himself or herself when touching the housing 14. The holes 31 are in close proximity to the slits 37, thereby preventing a substantial amount of the vaporized material from becoming part of the insulating air pocket 65, while still allowing the negative pressure created by a user's inhalation to create a partial vacuum in the air pocket 65 to enhance its insulating property.

By forming the air pocket 65 between the ceramic cup 22 and the housing 14 and using a user's inhalation to create a partial vacuum within the air pocket 65, the present invention provides a safer and longer-lasting device. By using a vaporizing chamber 59 separated from the hottest portion of the ceramic cup 22 by an air pocket 72 and a screen 70, but also allowing direct contact with the cylindrical walls 69 which are attached to the hottest portion of the ceramic cup 22, the bottom 67, the device also evenly heats the material within the vaporizing chamber 59 such that it is efficiently vaporized without creating harmful oxidative combustion byproducts. The vaporizer tank of the present invention is particularly suitable for vaporizing solid materials at variable temperatures, including very high temperatures.

Whereas, the present invention has been described in relation to the drawings attached hereto, it should be understood that other and further modifications, apart from those shown or suggested herein, may be made within the spirit and scope of this invention. Descriptions of the embodiments shown in the drawings should not be construed as limiting or defining the ordinary and plain meanings of the terms of the claims unless such is explicitly indicated.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The invention claimed is:

1. A variable temperature vaporizing tank comprising:
 a base having a bottom, a bolt configured to engage a vaporizer extending downward from the bottom, a top, and a cylindrical sleeve extending upward from the top;
 a housing defined by a cylindrical wall and a hemispherical top, wherein the cylindrical wall removably attaches to the base and the hemispherical top has a hole;
 a ceramic cup seated inside the cylindrical sleeve of the base, the ceramic cup having a flat bottom and a cylindrical wall extending upwardly to a rim, the ceramic cup defining a vaporizing chamber and a first air pocket, wherein the first air pocket is adjacent to the bottom of the ceramic cup and is separated from the vaporizing chamber by a screen, and the vaporizing chamber extends from the screen to the rim of the ceramic cup;
 a heating element in the base and abutting the bottom of the ceramic cup, wherein the heating element is not in direct contact with the cylindrical wall of the ceramic cup;
 one or more air inlet channels extending from one or more air inlets in the base, through the heating element, and into the air pocket at the bottom of the ceramic cup;
 a mouthpiece at a distal end of the housing having a cylindrical cuff, the cuff extending housing through the hole in the top of the housing;
 a bracket inside the housing removably attached to the cylindrical cuff of the mouthpiece, the bracket including a downwardly biased circular press plate, the bracket providing fluid communication between the inside of the housing and the mouthpiece, wherein the press plate extends partially into the vaporizing chamber;
 a second air pocket between the housing and the cylindrical wall of the ceramic cup.

2. The variable temperature vaporizing tank of claim 1 further comprising one or more O-rings extending about a circumference of the sleeve of the base, wherein the housing removably attaches by the cylindrical wall of the housing forming a friction fit with the O-rings.

3. The variable temperature vaporizing tank of claim 1 wherein the bracket includes a cuff extending downward and concentric with the vaporizing chamber.

4. The variable temperature vaporizing tank of claim 2 wherein the second air pocket is in fluid communication with the vaporizing chamber and the mouthpiece.

5. The variable temperature vaporizing tank of claim 2 further comprises a top seat threadably engaged with the bracket, extending through the hole in the hemispherical top of the housing, and forming a friction fit with the mouthpiece.

* * * * *